Oct. 11, 1966 W. FLEMER III Plant Pat. 2,679
HAWTHORN TREE
Filed Aug. 30, 1965
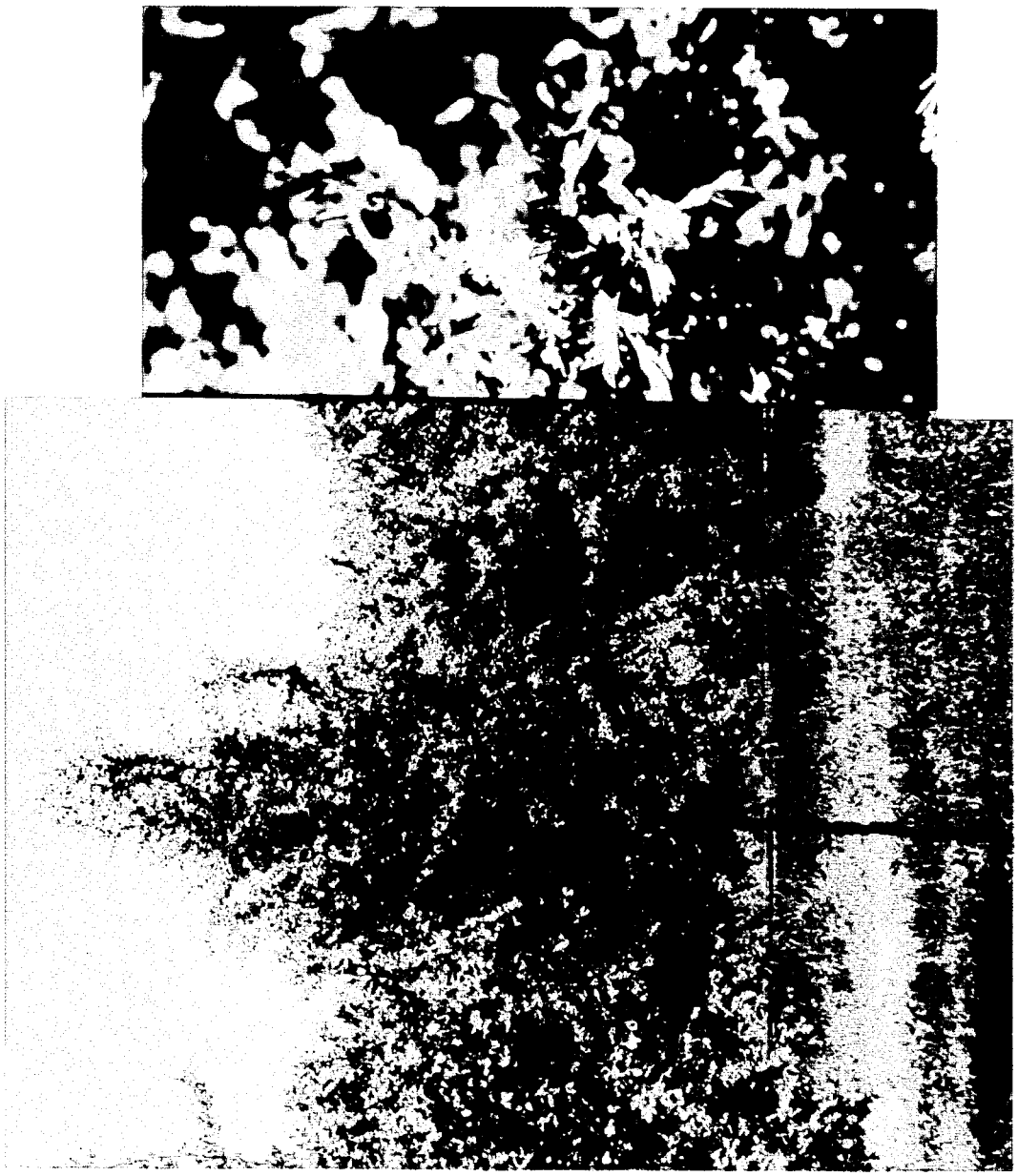
Inventor.
William Flemer, III
By: Robb & Robb
Attorneys.

United States Patent Office

Plant Pat. 2,679
Patented Oct. 11, 1966

2,679
HAWTHORN TREE

William Flemer III, Princeton, N.J., assignor to Princeton Nurserymen's Research Associates, Princeton, N.J., a partnership Filed Aug. 30, 1965, Ser. No. 483,894
1 Claim. (Cl. Plt.—51)

The present invention relates to a new and distinct variety of hawthorn tree (*Crataegus oxyacantha*) which was originated by me by crossing the hawthorn variety known as "Pauli" (unpatented) with the hawthorn variety known as "Charles X" (unpatented), the latter being the seed parent, and the former being the pollen parent.

As the result of this breeding, I have produced a new variety of hawthorn tree which is unique and is distinguished from its parents, as well as from all other varieties of which I am aware, as evidenced from the following combination of characteristics which are outstanding in the new variety:

(1) A shapely and upright habit of growth which is unusual in a normally straggling and spreading species;

(2) Flowers which are larger than those of its parent varieties;

(3) A distinctive and attractive clear bright red color of the flowers, with a white flower center; and (4) The production of glossy red fruit.

Asexual reproduction of my new variety by budding, sometimes called bud grafting, as performed by me in South Brunswick Township, New Jersey, shows that the foregoing characteristics and distinctions come true and are transmitted through succeeding propagations.

The accompanying drawing shows a typical specimen tree of my new hawthorn variety, as well as an enlarged fragmentary view showing typical specimen flowers and foliage, all as depicted in color as nearly true as it is reasonably possible to make the same in a color illustration of this character.

The following is a detailed description of my new variety, with color terminology in accordance with the Nickerson Color Fan, published by the Munsell Color Company, Inc., Baltimore, Maryland, except where general color terms of ordinary dictionary significance are obvious:

Parentage: Seedling.
*Male parent.*—*Crataegus oxyacantha* "Pauli."
*Female parent.*—*Crataegus oxyacantha* "Charles X."
Propagation: Holds its distinguishing characteristics through succeeding propagations by budding.

Locality where grown and observed: South Brunswick Township, New Jersey.
Tree: Small; upright; tall (about 25 feet); narrow.
*Trunk.*—Smooth. Color—Moderate Olive, Plate 5Y 4/3.
*Branches.*—Slender; smooth barked young branches; few short spines (from 6 cm. to 8 cm. long). Color.—Light Olive, Plate 5Y 5/6.
*Lenticles.*—Abundant; minute.
Foliage:
*Leaves.*—Abundant; small, thick. Length—from 5 cm. to 6 cm., including petiole. Width—from 4 cm. to 4½ cm. Shape—lobed; usually 5 large obtuse lobes with serrate margins. Color—Moderate Olive Green, Plate 5GY 4/3. Stipules—large; branched; serrate.
Flower buds: Hardy; small; globose. Color—Olive Brown.
Flowers:
*First open.*—About May 18.
*Full open.*—About May 20.
*Quantity.*—Normal for *Crataegus oxyacantha.*
*Size.*—Large (from 1¾ cm. to 2 cm. in diameter); normally three flowers per pedicel.
*Borne.*—In umbellate clusters of 10 to 15 flowers per cluster.
*Petalage.*—Normally 5 but occasionally 6 petals; round petal shape; from .5 cm. to .6 cm. long; from .5 cm. to .6 cm. wide.
*Color.*—Strong Red, Plate 5R 4/12, with distinct white center.
Fruit: Borne in moderate quantity; sub-globose; about 1 cm. long; about .8 cm. wide. Color—Scarlet.

I claim:

A new and distinct variety of hawthorn tree, substantially as herein shown and described, characterized particularly as to novelty by the unique combination of a shapely and upright habit of growth which is unusual in a normally straggling and spreading species, flowers which are larger than those of its parent varieties, a distinctive and attractive clear bright red color of the flowers, with a white flower center, and the production of glossy red fruit.

No references cited.

ABRAHAM G. STONE, *Primary Examiner.*

R. E. BAGWILL, *Assistant Examiner.*